United States Patent
Dwivedi et al.

(10) Patent No.: US 8,933,123 B2
(45) Date of Patent: Jan. 13, 2015

(54) POLYMORPHIC FORMS OF O-DESMETHYL-VENLAFAXINE SUCCINATE

(75) Inventors: Shriprakash Dhar Dwivedi, Ahmedabad (IN); Ashok Prasad, Ahmedabad (IN); Rushikesh Udaykumar Roy, Ahmedabad (IN)

(73) Assignee: Cadila Healthcare Limited, Ahmedabad (IN)

( * ) Notice: Subject to any disclaimer, the term of this patent is extended or adjusted under 35 U.S.C. 154(b) by 130 days.

(21) Appl. No.: 13/252,387

(22) Filed: Oct. 4, 2011

(65) Prior Publication Data

US 2012/0264828 A1   Oct. 18, 2012

(30) Foreign Application Priority Data

Oct. 8, 2010   (IN) .......................... 2804/MUM/2010

(51) Int. Cl.
*A61K 31/205* (2006.01)
*C07C 215/64* (2006.01)
*A61K 31/137* (2006.01)
*C07C 55/10* (2006.01)

(52) U.S. Cl.
CPC ............. *C07C 215/64* (2013.01); *A61K 31/137* (2013.01); *C07C 55/10* (2013.01); *C07B 2200/13* (2013.01); *C07C 2101/14* (2013.01)

USPC ........... 514/554; 514/574; 514/654; 562/590; 564/336; 564/374

(58) Field of Classification Search
None
See application file for complete search history.

(56) References Cited

U.S. PATENT DOCUMENTS

| | | | |
|---|---|---|---|
| 2008/0188567 A1 | 8/2008 | Huang et al. | |
| 2009/0246284 A1 | 10/2009 | Sebastian et al. | |
| 2011/0184067 A1* | 7/2011 | Pandya et al. | ................. 514/574 |

FOREIGN PATENT DOCUMENTS

WO   02/064543 A2   8/2002

OTHER PUBLICATIONS

Preliminary Report on Patentability dated Apr. 18, 2013 for Application No. PCT/IN2011/000695.
Wall, G. Michael, "Pharmaceutical Applications of Drug Crystal Studies", Pharmaceutical manufacturing, Feb. 1986, pp. 33-42.
Byrn, Stephen, et al., "Pharmaceutical Solids: A Strategic Approach to Regulatory Considerations", Pharmaceutical Research, vol. 12, No. 7, 1995, pp. 945-954.

* cited by examiner

*Primary Examiner* — Sudhakar Katakam
(74) *Attorney, Agent, or Firm* — Ladas & Parry LLP

(57) ABSTRACT

The present invention discloses polymorphic forms of O-desmethyl-venlafaxine succinate and processes for the preparation thereof.

16 Claims, 9 Drawing Sheets

POLYMORPHIC FORMS OF O-DESMETHYL-VENLAFAXINE SUCCINATE

FIELD OF THE INVENTION

The invention relates to polymorphic forms of O-desmethyl-venlafaxine succinate. More particularly, it relates to stable crystalline forms of O-desmethyl-venlafaxine succinate designated as Form "Z" and Form "Z1", respectively and processes for their preparation. The invention also relates to pharmaceutical compositions that includes crystalline Form "Z" and Form "Z1" of O-desmethyl-venlafaxine succinate.

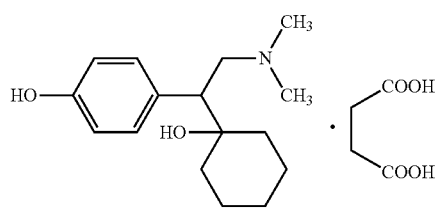

(I)

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Venlafaxine, (±)-1-[2-(Dimethylamino)-1-(4-ethyoxyphenyl)ethyl]cyclohexanol is the first of a class of anti-depressants. Venlafaxine acts by inhibiting re-uptake of norepinephrine and serotonin, and is an alternative to the tricylic anti-depressants and selective re-uptake inhibitors. Venlafaxine has the following structure of formula (II).

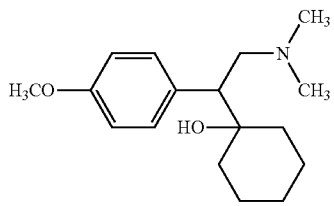

(II)

O-desmethyl-venlafaxine, 4-[2-(dimethylamino)-1-(1-hydroxycylcohexyl)ethyl]phenol, is a major metabolite of venlafaxine (Effexor) and has been shown to inhibit norepinephrine and serotonin uptake. See Klarnerus, K. J. et al., "Introduction of the composite parameter to the pharmacokinetics of venlafaxine and its active O-desmethyl metabolite," *J. Clin. Pharmacol.* 32:716-724 (1992). O-desmethyl-venlafaxine is also being targeted as the first non-hormonal based treatment for menopause represented by the following formula (I) is an active ingredient marketed under the proprietary name PRISTIQ®.

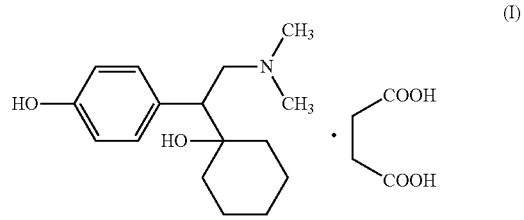 [SMILES: CN(C)CC(c1ccc(O)cc1)C1(O)CCCCC1 ; O=C(O)CCC(=O)O]

(I)

U.S. Pat. No. 4,535,186 discloses the process for the preparation of O-desmethyl-venlafaxine, which is shown in below mentioned scheme:

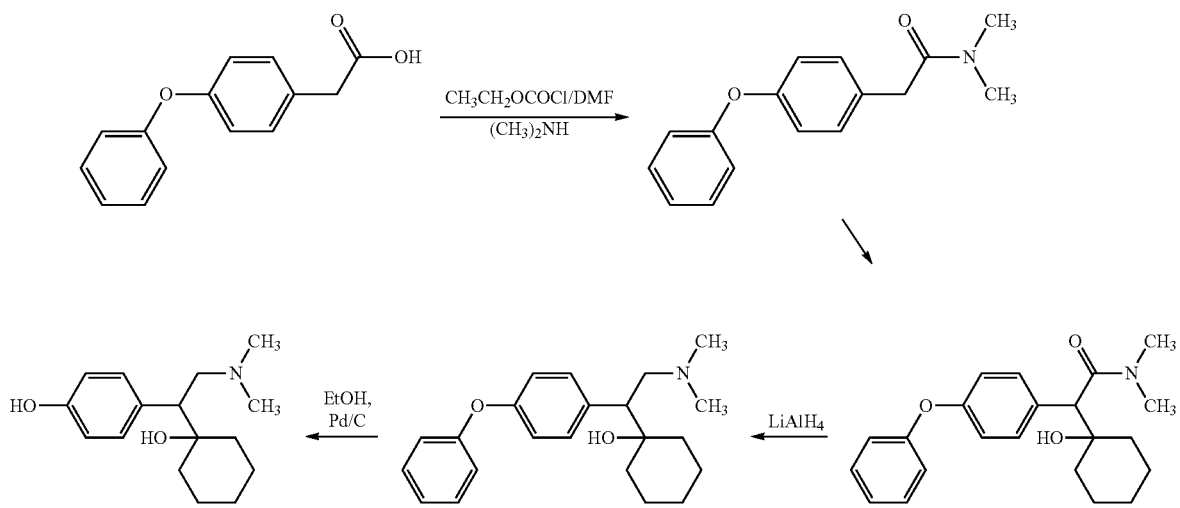

U.S. Pat. No. 5,043,466 discloses an improved process for preparing O-desmethyl-venlafaxine. U.S. Pat. No. 6,673,838 B2 (the U.S. Pat. No. '838 B2) discloses four crystalline forms and an amorphous form of O-desmethyl-venlafaxine succinate and processes for their preparation. In particular, the U.S. Pat. No. '838 B2 discloses two crystalline monohydrate forms designated as Form I and Form II, respectively; one crystalline hydrated form designated as Form III with a water content between hemihydrate and monohydrate; one crystalline anhydrous form designated as Form IV and an amorphous form of O-desmethyl-venlafaxine succinate.

U.S. Pat. No. 6,197,828 B2 discloses O-desmethyl-venlafaxine succinate in substantially pure form. U.S. Patent Application No. 2004/0180952 A1 discloses the process for preparation of O-desmethyl-venlafaxine by demethylation of venlafaxine with lithium diphenylphosphide.

Several processes for the preparation of O-desmethyl-venlafaxine have been disclosed, for example like U.S. Patent Application Nos. 2004/0158901 A1, 2007/0149813 A1, 2007/0299283 A1, 2008/0015259 A1, 2009/0246284 A1 and U.S. Pat. No. 7,179,944 B2.

International (PCT) Publication WO 2008/013995 A1 discloses process for the preparation O-desmethyl-venlafaxine succinate which is incorporated herein as a reference in its entirety.

Several crystalline forms of O-desmethylvenlafaxine succinate and their processes for preparation have been disclosed, for example like U.S. Pat. No. 7,820,716 B2, U.S. Patent Application No. 2011/0184067 A1, International (PCT) Publication Nos. WO 2008/017886 A1, WO 2008/047167 A1, WO 2008/110338A1, WO 2008/156748 A2, WO 2009/009665 A2, WO 2009/010990 A2, WO 2009/027766 A1 and WO 2009/118758 A2.

U.S. Pat. No. 7,674,935 B2 discloses crytalline Form-A, Form-C and Form-D of O-desmethyl-venlafaxine base.

Polymorphism is the occurrence of different crystalline forms of a single compound and it is a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as different solubility profiles, different melting point temperatures and/or different x-ray diffraction peaks. Since the solubility of each polymorph may vary, identifying the existence of pharmaceutical polymorphs is essential for providing pharmaceuticals with predicable solubility profiles. It is desirable to investigate all solid-state forms of a drug, including all polymorphic forms, and to determine the stability, dissolution and flow properties of each polymorphic form. The polymorphic forms of a compound can be distinguished in a laboratory by X-ray diffraction spectroscopy and by other methods such as, infrared spectrometry. For a general review of polymorphs and the pharmaceutical applications of polymorphs, See G. M. Wall, Pharm Manuf. 3, 33 (1986); J. K. Haleblian and W. McCrone, J. Pharm. Sci., 58, 911 (1969); and J. K. Haleblian, J. Pharm. Sci., 64, 1269 (1975), all of which are incorporated herein by reference.

The known crystalline forms of O-desmethyl-venlafaxine succinate are hydrates, which are very susceptible in presence of water. They are the hydrates like monohydrates, hemihydrates, anhydrous or even amorphous compounds. Therefore, the present invention provides new crystalline forms of O-desmethyl-venlafaxine succinate, which are stable and useful for pharmaceutical compositions that include the crystalline O-desmethyl-venlafaxine succinate.

SUMMARY OF THE INVENTION

The inventors have discovered novel crystalline polymorphic forms of O-desmethyl-venlafaxine and have developed processes for the preparation of the crystalline form. The new crystalline forms of O-desmethyl-venlafaxine succinate of Formula (I) are designated as Form "Z" and Form "Z1", respectively.

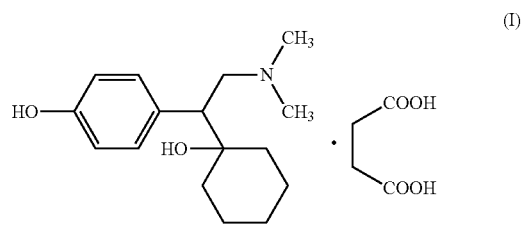 [SMILES: CN(C)CC(c1ccc(O)cc1)C1(O)CCCCC1 ; O=C(O)CCC(=O)O]

In one general aspect there is provided a novel crystalline Form of O-desmethyl-venlafaxine succinate designated as Form "Z".

In another general aspect there is provided a novel crystalline Form of O-desmethyl-venlafaxine succinate designated as Form "Z1".

The Form "Z" of O-desmethyl-venlafaxine succinate may have the X-ray diffraction pattern of FIG. 1, differential scanning calorimetry thermogram of FIG. 2, TGA analysis of FIG. 3 and infrared spectrum of FIG. 4.

The Form "Z1" of O-desmethyl-venlafaxine succinate may have the X-ray diffraction pattern of FIG. 7, differential scanning calorimetry thermogram of FIG. 8, and Solid States $^{13}$C NMR of FIG. 9.

In one general aspect there is provided a process for the preparation of crystalline Form "Z" of O-desmethyl-venlafaxine succinate. The process includes grinding a solid-solid mixture of substantially anhydrous O-desmethyl-venlafaxine free base and succinic acid in a grinder for sufficient time and interval and isolating O-desmethyl-venlafaxine succinate Form "Z".

Embodiments of the process may include one or more of the following features. For example, the solid-solid mixture of substantially anhydrous O-desmethyl-venlafaxine free base and succinic acid may be added in grinder; grinding the solid-solid mixture below about 60° C. for less than about 2 minutes, followed by repeating the grinding cycles.

In another general aspect, the crystalline Form "A" of O-desmethyl-venlafaxine free base is characterized by the X-ray diffraction pattern as shown in FIG. 5, differential scanning calorimetry thermogram as shown in FIG. 6.

In another general aspect there is provided a process for the preparation of crystalline Form "Z1" of O-desmethyl-venlafaxine succinate. The process includes grinding a solid-solid mixture of substantially anhydrous O-desmethyl-venlafaxine free base and succinic acid under controlled humidity in a grinder for sufficient time and interval and isolating O-desmethyl-venlafaxine succinate Form "Z1".

Embodiments of the process may include one or more of the following features. For example, the solid-solid mixture of substantially anhydrous O-desmethyl-venlafaxine free base and succinic acid may be added in grinder under controlled humidity conditions; adjusting the blades and scrappers moving in sharper edge side in clockwise direction; grinding the solid-solid mixture below about 60° C. for less than about 2 minutes, followed by repeating the grinding cycles.

In another general aspect there is provided a pharmaceutical composition that includes a therapeutically effective amount of the crystalline Form "Z" of O-desmethyl-venlafaxine succinate; and one or more pharmaceutically acceptable carriers, excipients or diluents.

In another general aspect there is provided a pharmaceutical composition that includes a therapeutically effective amount of the crystalline Form "Z1" of O-desmethyl-venlafaxine succinate; and one or more pharmaceutically acceptable carriers, excipients or diluents.

In another general aspect there is provided a stable crystalline Form "Z" of O-desmethyl-venlafaxine succinate having water content from about 1.0% to about 3.5% w/w.

In another general aspect there is provided a stable crystalline Form "Z1" of O-desmethyl-venlafaxine succinate having water content from about 1.0% to about 2.0% w/w.

The details of one or more embodiments of the inventions are set forth in the description below. Other features, objects and advantages of the inventions will be apparent from the description.

BRIEF DESCRIPTION OF THE ACCOMPANYING DRAWINGS

FIG. 1—represents the PXRD of Form Z of O-desmethyl-venlafaxine succinate.

FIG. 2—represents the DSC of Form Z of O-desmethyl-venlafaxine succinate.

FIG. 3—represents the TGA of Form Z of O-desmethyl-venlafaxine succinate.

FIG. 4—represents the IR of Form Z of O-desmethyl-venlafaxine succinate.

FIG. 5—represents the PXRD of Form A of O-desmethyl-venlafaxine free base.

FIG. 6—represents the DSC of Form A of O-desmethyl-venlafaxine free base.

FIG. 7—represents the PXRD of Form Z1 of O-desmethyl-venlafaxine succinate.

FIG. 8—represents the DSC of Form Z1 of O-desmethyl-venlafaxine succinate.

FIG. 9—represents the Solid States $^{13}$C NMR of Form Z1 of O-desmethyl-venlafaxine succinate.

DETAILED DESCRIPTION OF THE INVENTION

The inventors have found new polymorphic forms of O-desmethyl-venlafaxine succinate and, in particular, the crystalline form designated as Form "Z" and "Z1" of O-desmethyl-venlafaxine succinate. The new crystalline Form "Z" is characterized by its X-ray powder diffraction pattern, differential scanning calorimetry thermogram, thermal analysis and infrared spectrum as shown in FIGS. 1, 2, 3 and 4, respectively. The new crystalline Form "Z1" is characterized by its X-ray powder diffraction pattern, differential scanning calorimetry thermogram, and solid states $^{13}$C NMR as shown in FIGS. 7, 8, and 9, respectively.

The inventors also have developed a process for the preparation of the crystalline Form "Z" of O-desmethyl-venlafaxine succinate, by adding a solid-solid mixture of O-desmethyl-venlafaxine free base and succinic acid in a grinder and grinding the solid-solid mixture to obtain the crystalline Form Z of O-desmethyl-venlafaxine succinate.

The inventors also have developed a process for the preparation of the crystalline Form "Z1" of O-desmethyl-venlafaxine succinate, by adding a solid-solid mixture of O-desmethyl-venlafaxine free base and succinic acid in a grinder and grinding the solid-solid mixture under controlled humidity to obtain the crystalline Form "Z1" of O-desmethyl-venlafaxine succinate.

All ranges recited herein include the endpoints, including those that recite a range "between" two values. Terms such as "about", "general", "substantially" and the like are to be construed as modifying a term or value such that it is not an absolute. Such terms will be defined by the circumstances and the terms that they modify as those terms are understood by those skill in the art. This includes, at very least, the degree of expected experimental error, technique error and instrument error for a given technique used to measure a value.

The term "controlled humidity" refers to a relative humidity in the range of 50±10%. In particular, the controlled humidity includes grinding process performed under controlled humidity followed by drying under controlled humidity for the preparation of crystalline Form "Z1" of O-desmethyl-venlafaxine succinate.

The product obtained may be further dried to achieve the desired moisture values. For example, the product may be dried in a tray drier, dried under vacuum and/or in a Fluid Bed Drier.

As used herein, the term "grinder" includes mixers, mills, blenders, micronizers, and the like or a combination thereof. The terms "grinding", "milling", "mixing", "blending" and the like are interchangeable for achieving the homogeneous solid-solid mixture.

In general, crystalline Form "Z" of O-desmethyl-venlafaxine succinate may be obtained by grinding O-desmethyl-venlafaxine free base and succinic acid together in a grinding apparatus. O-desmethyl-venlafaxine free base used as starting material may be prepared in crystalline Form-A by the methods disclosed in the U.S. Patents or Patent Applications mentioned hereinbefore, which are incorporated herein by reference.

Embodiments of the process may comprises of forming a mixture of O-desmethyl-venlafaxine free base and succinic acid, and subjecting the mixture to grinding action, wherein a composition is obtained in which the O-desmethyl-venlafaxine has a purity by HPLC analysis of at least 99%, and the O-desmethyl-venlafaxine succinate is substantially free of any other crystalline forms.

In one general aspect, a solid-solid mixture of O-desmethyl-venlafaxine and succinic acid may be milled by grinding action between two surfaces. Such milling has been traditionally carried out in pharmacy practice by compounding using a pestle and mortar or a common mixer grinder. According to the invention milling machines that work on substantially the same principle may be used in the present process. Examples of such milling machines include various makes of ball mills, roller mills, gyratory mills, multi-mills, Jet-mills, and the like.

In a preferred aspect, a mill such as a Micros Super Fine Mill (available from Nara Machinery Co. Ltd or Tokyo, Japan), Multi-Mill Sr. No. G. 1.132 (available from Grooves International Pharmaceutical & Chemical Machinery), Jet-Mill from Midas Micronizer M-100 Aerosol (No. 154/07-08 (available from microtech Engineering Company) or a common mixer grinder can be used. Alternatively another commercially available milling machine can be used.

The process parameter includes adding a solid-solid mixture of O-desmethyl-venlafaxine free base and succinic acid in a grinder. A specific grinder used can be small-scale to large-scale mixer grinder which can easily prepare the homogeneous mixture of two solids. For example purpose, Quadro dry mixing apparatus for providing lump-free homogenous blending to ensure proper mixing.

This grinding apparatus may consists of a water cooled jacketed bowl with the inside surface made of a suitable material such as Zirconium oxide, stainless steel, tungsten carbide, or aluminum oxide. Depending on the size of the grinder, the speed of rotation of the main shaft and the effective volume of the grinding chamber may vary. The effective volume of the grinding chamber may be in the range from about 0.45 liters to about 30 liters. For low capacity mills (such as 0, capacity 0.45 liters; or 5, capacity 4.8 liters), the speed of rotation of the main shaft is typically in the range from about 500 rpm to about 2000 rpm.

In general, the grinder may be a typical milling apparatus. This milling apparatus may be typically charged with feed material such that from about 10% to 30% of the effective volume of the grinding chamber is occupied. Examples of methods of transferring materials well known in the art include manual transfer, gravity feed, pneumatic conveying (using a high velocity air stream), and vacuum transfer. Such methods, well known in the art, may be used with the process of this invention to charge the feed material into the grinding volume available between the bowl and the subshafts. For obtaining homogeneous solid-solid mixture, the O-desmethyl-venlafaxine free base and succinic acid may be mixed in a wide range of ratios, for example, from about 1:20 to about 100:1; however, in preferred embodiments of the invention, the ratio of free base to acid is from about 24:1 to about 2:1, more preferably from about 15:1 to about 5:1.

The period of milling using the mill may vary depending on the size of the mill, the speed of rotation of the main shaft, the type of feed material, and the quantity of feed material. The effects of these variables are well known in the art and the invention may be worked over a range of these variables. Typically, the period of milling ranges from about 15 minutes to 300 minutes.

According to another aspect of the invention, the O-desmethyl-venlafaxine succinate is subjected to grinding involving attrition of the particles and machine surfaces.

According to one general aspect, there is provided a novel crystalline Form "Z" of O-desmethyl-venlafaxine succinate of formula (I).

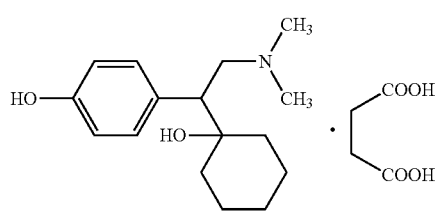

The novel crystalline Form "Z" of O-desmethyl-venlafaxine succinate characterized by X-ray powder diffraction with characteristics peaks, (a) having relative intensity greater than 50% at about 15.8, 16.5, 19.9, and 25.8 degrees; or (b) having relative intensity greater than 35% at about 13.1, 14.2, 17.5, 19.2, and 20.3 degrees (2θ); or combination of (a) and (b).

The novel crystalline Form "Z" of O-desmethyl-venlafaxine succinate may be characterized by its powder X-ray diffraction pattern as shown in FIG. 1. The crystalline Form "Z" of O-desmethyl-venlafaxine succinate is characterized by its powder X-ray diffraction pattern having peaks expressed as 2θ at about 5.0, 10.1, 12.0, 13.1, 14.2, 15.8, 16.5, 17.5, 19.2, 19.9, 20.3, 22.3, 23.6, 24.5, 25.8, 26.5, and 31.4 degrees.

Figure 1:
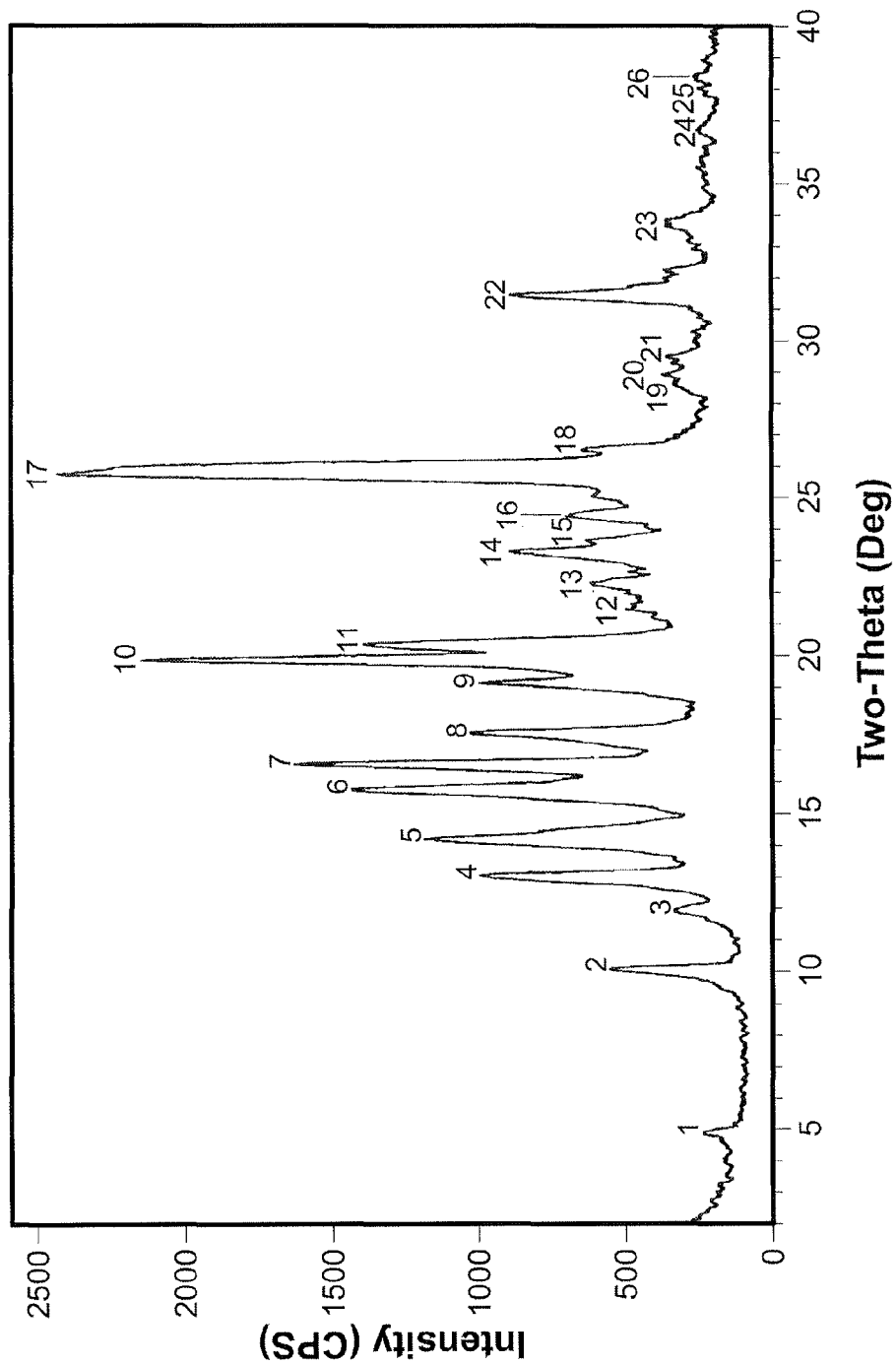
Figure 2:
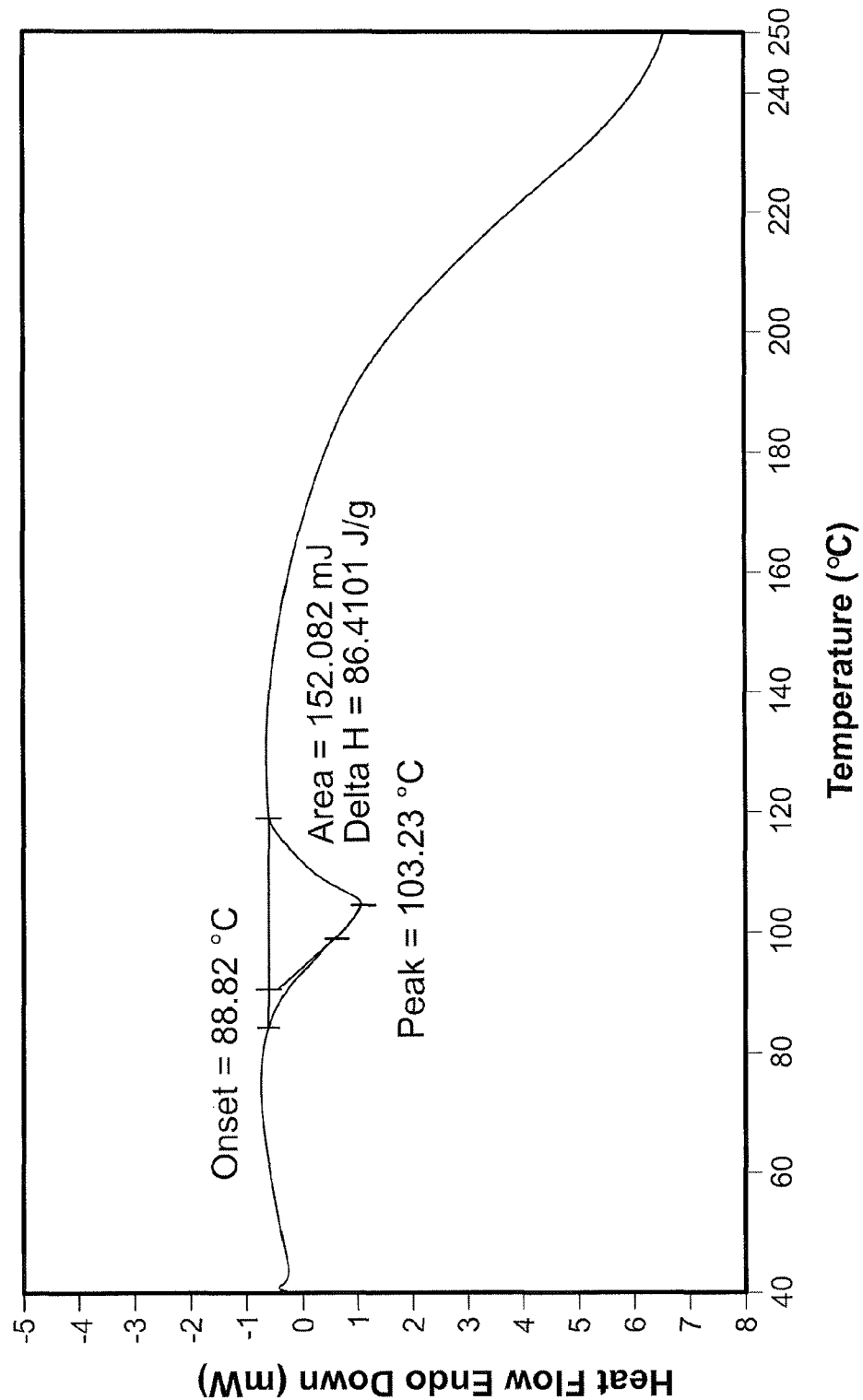
FIG. 2 shows DSC analysis of typical Form "Z" of O-desmethyl-venlafaxine succinate. The crystalline Form "Z" of O-desmethyl-venlafaxine succinate is characterized by an endotherm at about 103.23° C. in DSC analysis.
Figure 3:
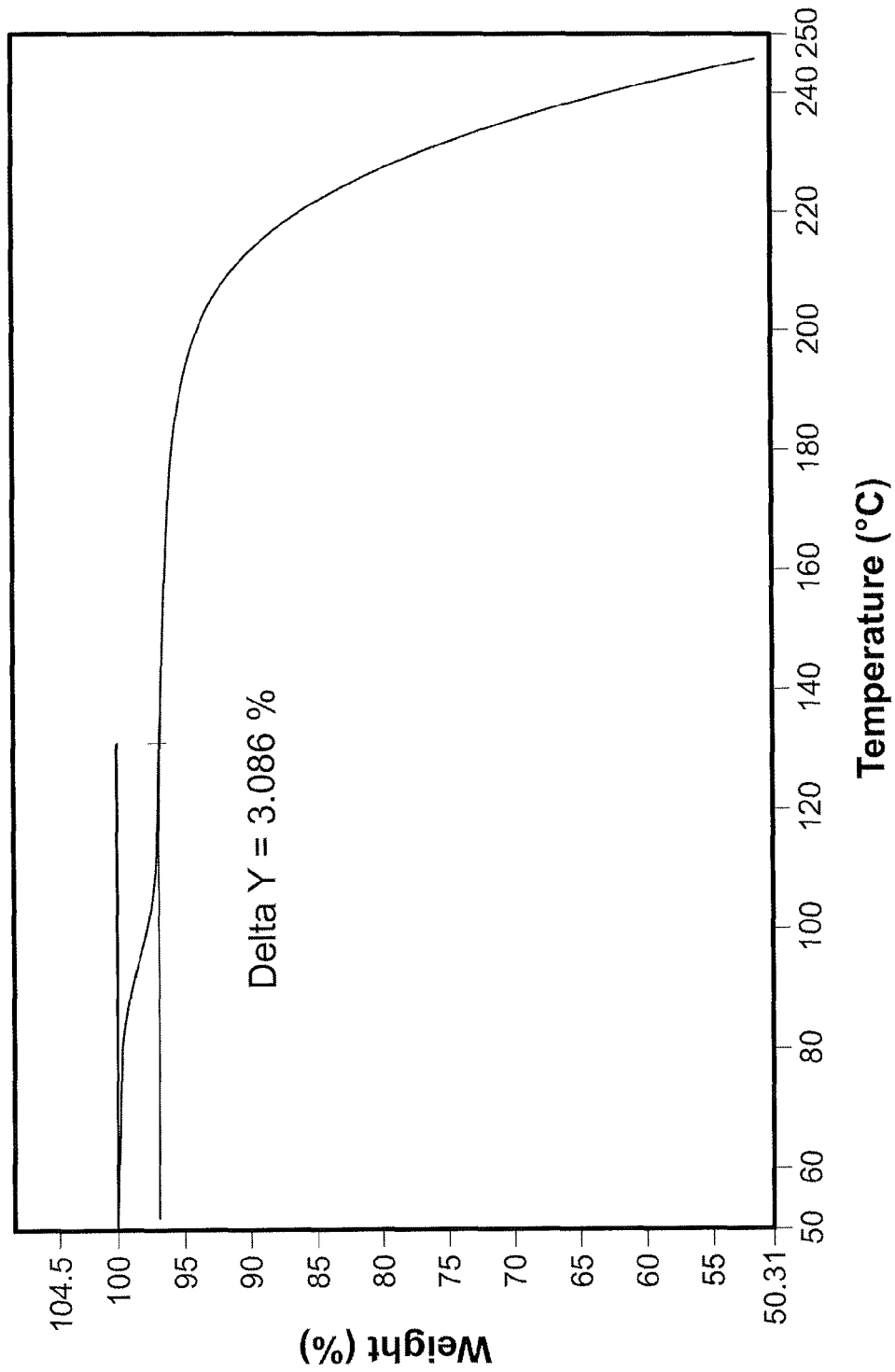
FIG. 3 represents the thermogravimetric analysis of Form "Z" of O-desmethyl-venlafaxine succinate, which shown weight loss of about 3.08%.

The crystalline Form "Z" of O-desmethyl-venlafaxine succinate of present invention having water content from about 1.0% to about 3.5% w/w, when analyzed by KF.

In one general aspect, there is provided a process for preparation of crystalline Form "Z" of O-desmethyl-venlafaxine succinate, the process comprises:
(a) adding solid-solid mixture of O-desmethyl-venlafaxine free base and succinic acid in grinder;
(b) grinding the solid-solid mixture to obtain crystalline Form "Z" of O-desmethyl-venlafaxine succinate.

Embodiments of the process includes, grinding a solid-solid reaction mixture of O-desmethyl-venlafaxine free base and succinic acid in absence of solvents. Further the grinding may be performed below 60° C. The grinding cycles may be repeated for one or more times. The reaction being an exothermic reaction, results in rise of temperature. In general, such a mixture may be cooled below 60° C. and again the solid-solid reaction mixture is grinded below 60° C. The repetition of about 25-35 such grinding cycles followed by cooling results in crystalline Form "Z" of O-desmethyl-venlafaxine succinate.

The process parameter includes adding O-desmethyl-venlafaxine free base and succinic acid in a grinder. A specific grinder used can be small-scale to large-scale mixer grinder which can easily prepare the homogeneous mixture of two solids. For example purpose, batch mixers like change-can mixers, Helical-Blade mixers, Double-Arm Kneading Mixers, continuous mixers, Intensive mixers and the like, Mills like multi-mill, jet-mill, ball-mill, hammer mills, and the like, Quadro dry mixing apparatus for providing lump-free homogenous blending to ensure proper mixing. The varieties of mills and mixers provided in *Perry's Chemical Engineers' Handbook* Seventh Edition by Robert H. Perry and Don W. Green can be used based on suitability are incorporated herein by reference in its entirety.

In preferred general aspect, the O-desmethyl-venlafaxine free base and succinic acid are grinded to a homogeneous solid-solid mixture in absence of solvents with continuous grinding below 60° C. In particular, it was grinded at about 50° C. to 55° C. The time interval may vary from about 1 minute to about 2 minutes. In particular, the reaction may be grinded for about 1.5 minutes.

During the grinding of solid compounds, strong exothermicity may be observed. In general, the mixture may be cooled to less than 45° C., particularly to 38° C. to 42° C. Again the mixture may be heated to less than 60° C., particularly at about 50° C. to 55° C. The mixture may be cooled to less than 45° C., particularly to 38° C. to 42° C. This grinding cycle may be repeated for one or more times. In particular for about 25 to about 35 times for obtaining crystalline Form "Z" of O-desmethylvenlafaxine succinate as monitored by X-ray powder diffraction.

In general, O-desmethyl-venlafaxine free base and succinic acid used for solid-solid interaction should be substantially anhydrous, particularly having water content less than about 0.5% wt/wt, more particularly less than about 0.4%, most particularly, less than about 0.3% wt/wt.

Thus, by controlling the water content during the reaction monitoring it was possible to obtain O-desmethyl-venlafaxine succinate crystalline Form "Z" substantially free from Form-I and Form-II being monohydrate forms.

In another general aspect there is provided a pharmaceutical composition that includes a therapeutically effective amount of the crystalline Form "Z" of O-desmethyl-venlafaxine succinate; and one or more pharmaceutically acceptable carriers, excipients or diluents.

Figure 5:
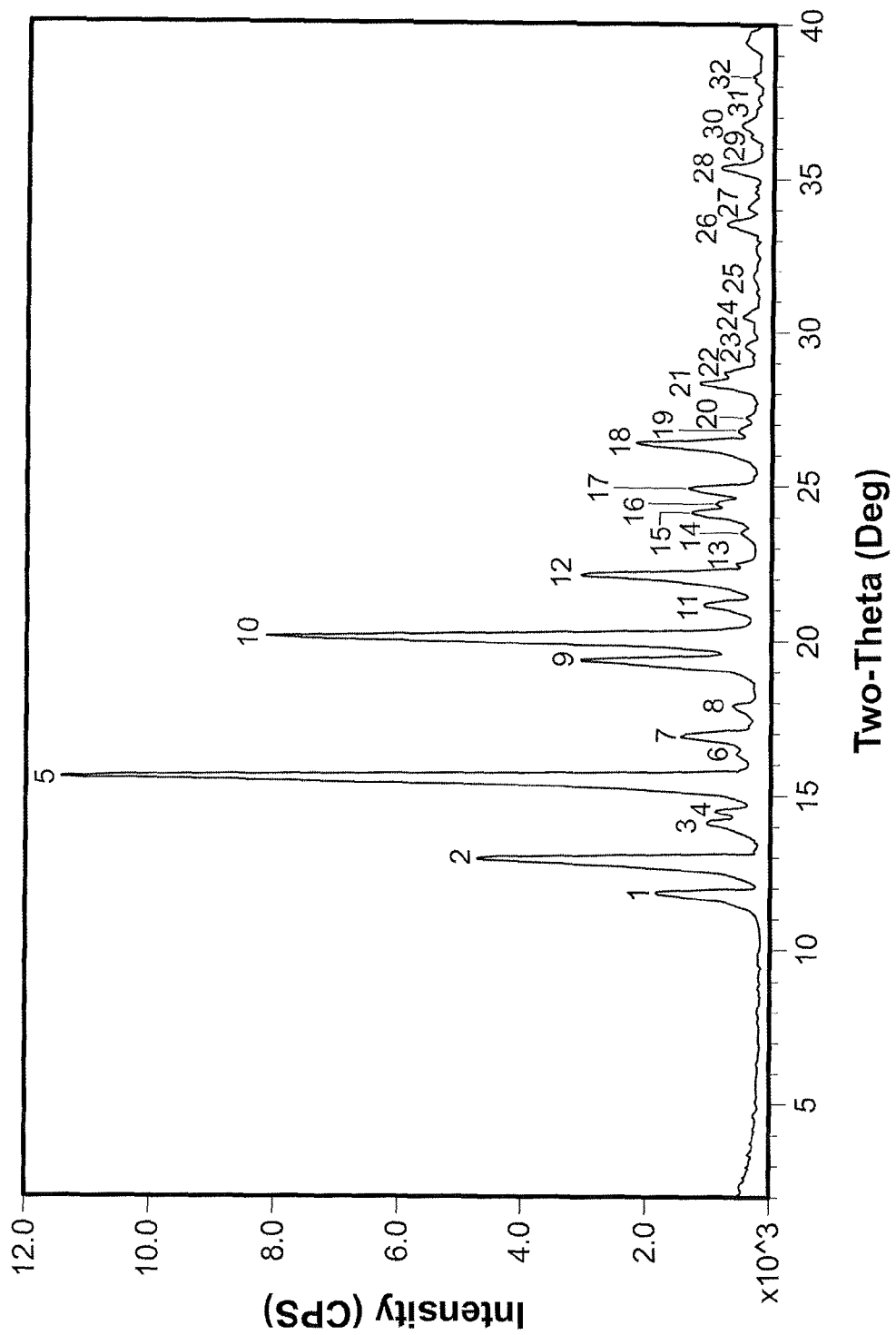

In another general aspect, the crystalline Form-A of O-desmethyl-venlafaxine free base used for preparing novel crystalline forms of O-desmethyl-venlafaxine succinate may be characterized by X-ray powder diffraction pattern having peaks expressed as 2θ at about 12.1, 13.1, 15.9, 19.7, 20.4, and 22.4 degrees. Form-A of O-desmethyl-venlafaxine free base is also characterized by X-ray powder diffraction patter substantially as depicted in FIG. 5.

Figure 6:
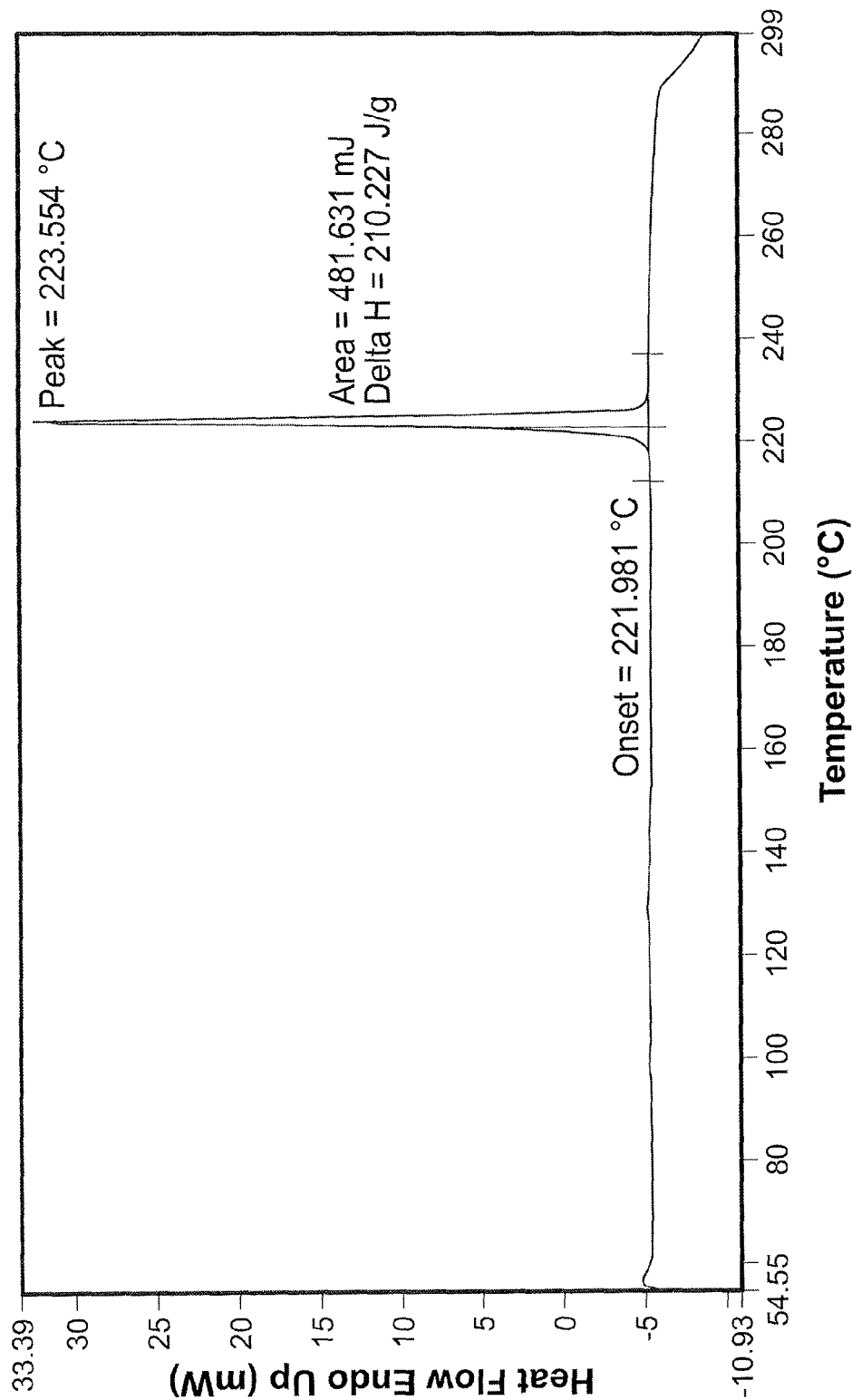

In general, Form-A of O-desmethyl-venlafaxine free base can also be characterized by differentially scanning calorimetery (DSC) having an endotherm at about 223.5° C. and substantially as depicted in FIG. 6.

In another general aspect, there is provided a novel crystalline Form "Z1" of O-desmethyl-venlafaxine succinate of formula (I).

Figure 7:
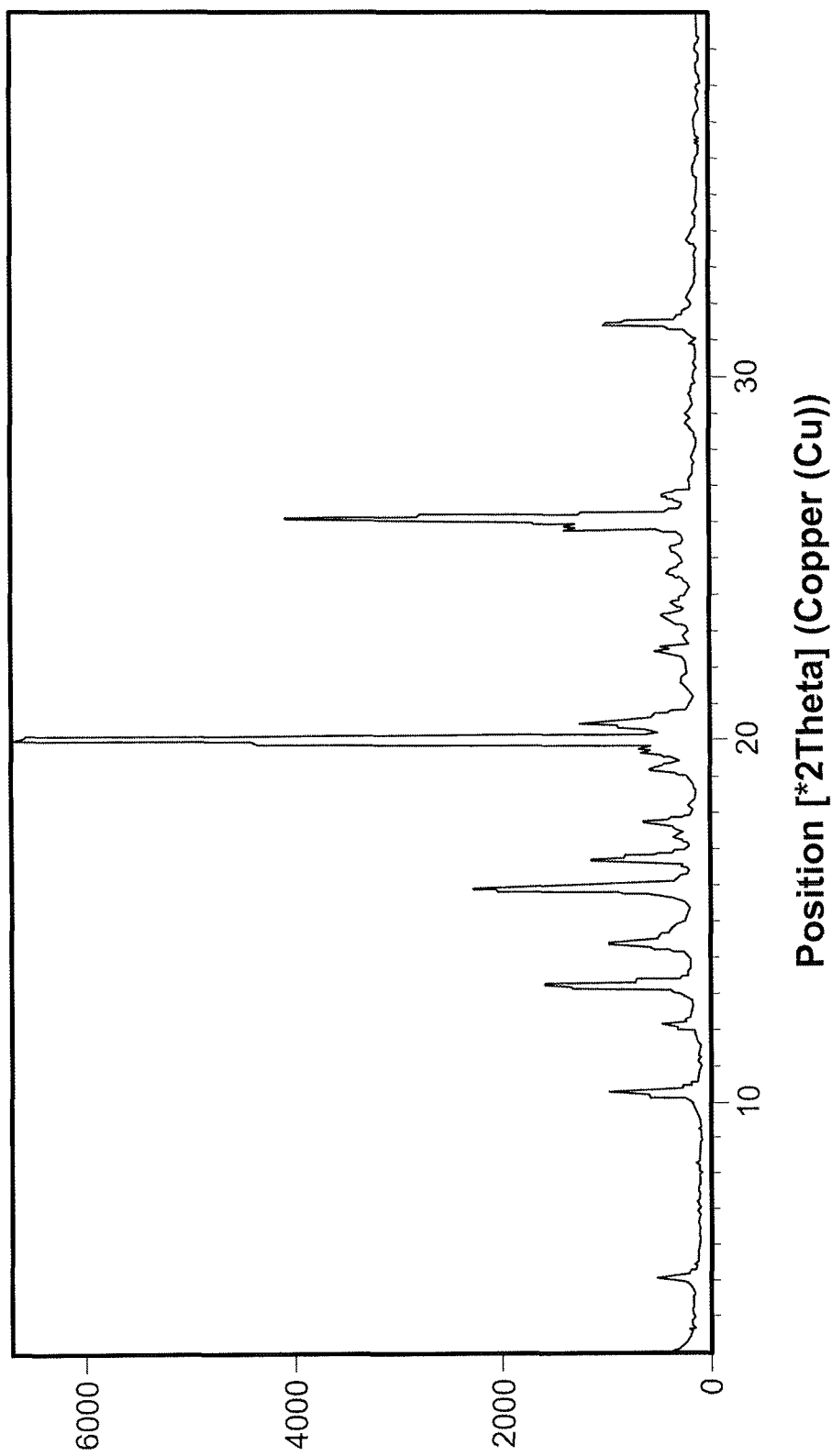

The novel crystalline Form "Z1" of O-desmethyl-venlafaxine succinate may be characterized by its powder X-ray diffraction pattern as shown in FIG. 7. The crystalline Form "Z1" of O-desmethyl-venlafaxine succinate is also characterized by its powder X-ray diffraction pattern having peaks expressed as 2θ at about 5.1, 10.3, 12.1, 13.3, 14.3, 15.9, 16.7, 17.7, 19.2, 20.0, 20.4, 23.3, 24.5, 25.2, 25.9, 26.7 and 31.4 degrees.

Figure 8:
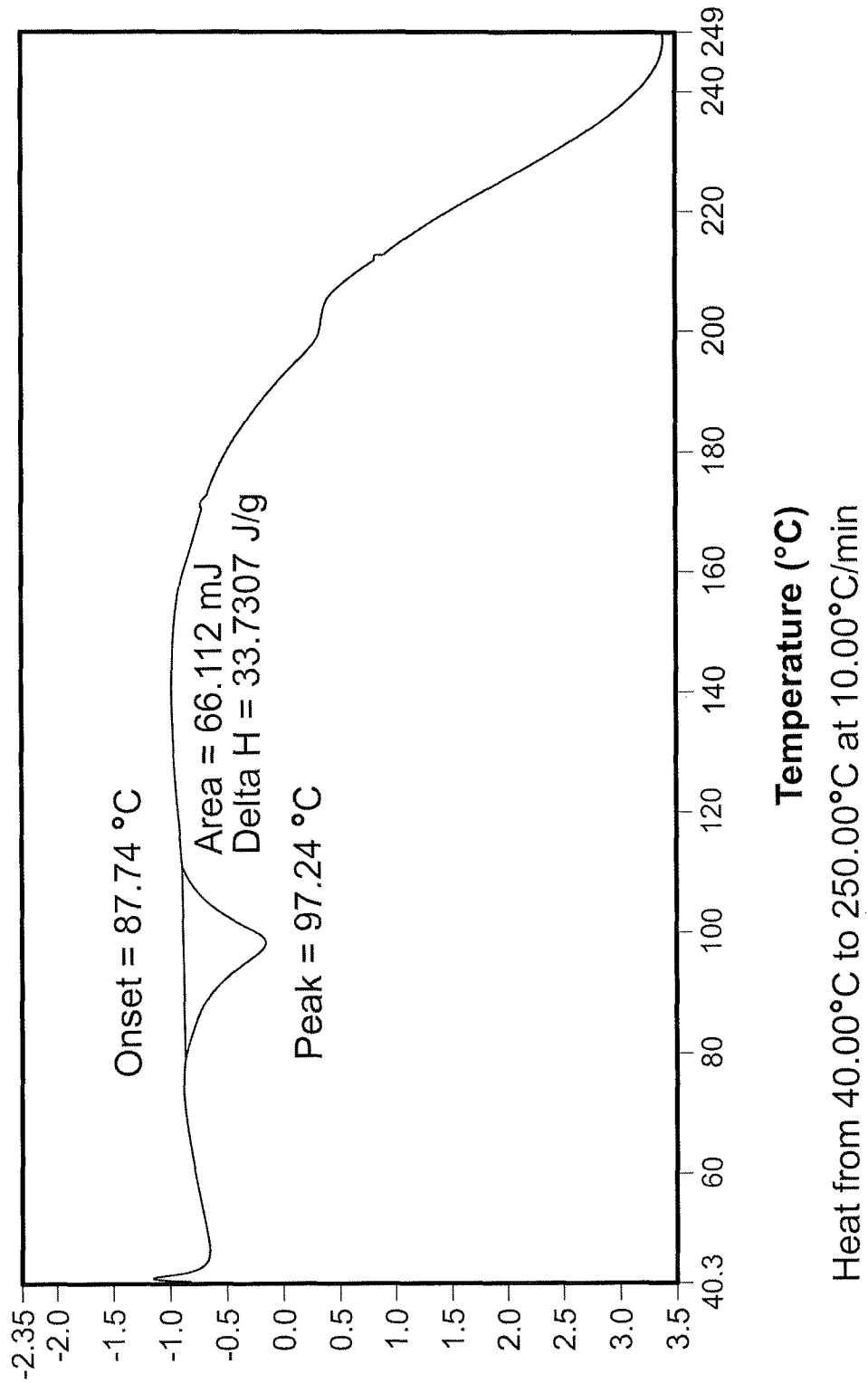

FIG. 8 shows DSC analysis of typical Form "Z1" of O-desmethyl-venlafaxine succinate. The crystalline Form "Z1" of O-desmethyl-venlafaxine succinate is characterized by an endotherm at about 97.24° C. in DSC analysis.

Figure 9:
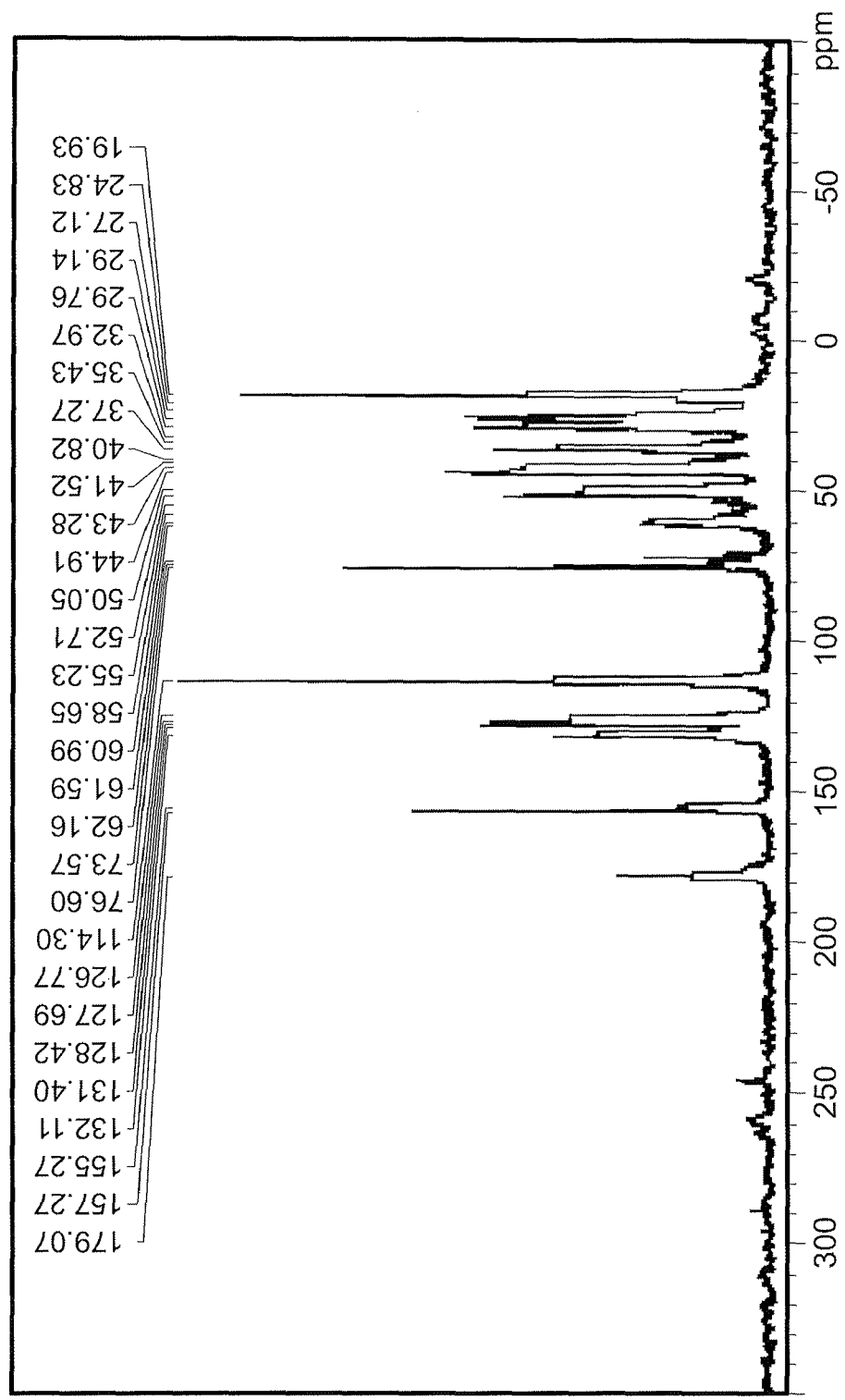

FIG. 9 represents the solid-states $^{13}$C nuclear magnetic resonance of crystalline Form "Z1" of O-desmethyl-venlafaxine succinate having the following chemical shifts expressed in parts per million at about 19.9, 24.8, 27.1, 29.1, 29.7, 32.9, 35.4, 37.2, 40.7, 41.5, 43.2, 44.9, 50.0, 52.7, 55.2, 58.6, 61.0, 61.6, 62.1, 73.5, 76.6, 114.3, 126.7, 126.7, 127.7, 128.4, 131.4, 132.11, 155.2 and 179.0.

The crystalline Form "Z1" of O-desmethyl-venlafaxine succinate of present invention having water content of about 1.0% to about 2.0% w/w, when analyzed by KF.

In another general aspect there is provided a process for the preparation of crystalline Form "Z1" of O-desmethyl-venlafaxine succinate, the process comprises:
  (a) adding a solid-solid mixture of O-desmethyl-venlafaxine free base and succinic acid in grinder; and
  (b) grinding the solid-solid mixture under controlled humidity to obtain crystalline Form "Z1" of O-desmethyl-venlafaxine succinate.

Embodiments of the process may include one or more of the following features. For example, the solid-solid mixture of O-desmethyl-venlafaxine free base and succinic acid may be added in grinder under controlled humidity conditions in absence of solvents; adjusting the blades and scrappers moving in sharper edge side in clockwise direction; grinding the solid-solid mixture below about 60° C. to obtain crystalline Form "Z1" of O-desmethyl-venlafaxine succinate.

In general, the grinding cycles may be repeated for one or more times under controlled humidity. The controlled humidity may be a relative humidity in the range of 50±10%. In particular, the grinding cycles may be repeated for about 25-35 times followed by cooling to obtain crystalline Form "Z1" of O-desmethyl-venlafaxine succinate. The time interval may vary from about 1 minute to about 2 minutes. In particular, the reaction may be grinded for about 1.5 minutes.

During the grinding of solid compounds, strong exothermicity may be observed. Therefore, the mixture may be cooled to less than 45° C., particularly to 38° C. to 42° C. Again the mixture may be heated to less than 60° C., particularly, at about at about 50° C. to 55° C. The mixture may be again cooled to less than 45° C., particularly to 38° C. to 42° C. These grinding cycles may be repeated from about 25 to about 35 times till the formation of crystalline Form "Z1" of O-desmethylvenlafaxine succinate as monitored by X-ray powder diffraction.

The Form "Z1" of O-desmethyl-venlafaxine succinate is having the X-ray diffraction pattern of FIG. 7, differential scanning calorimetry thermogram of FIG. 8, and Solid States $^{13}$C NMR of FIG. 9.

In general, O-desmethyl-venlafaxine free base and succinic acid used for solid-solid interaction should be substantially anhydrous, preferably having water content less than 0.5% wt/wt, more preferably less than 0.4%, still more preferably less than 0.3% wt/wt.

Thus, by controlling the water content during the reaction monitoring it was possible to obtain O-desmethyl-venlafaxine succinate crystalline Form "Z1" substantially free from Form-I and Form-II being monohydrate forms.

In another general aspect there is provided a pharmaceutical composition that includes a therapeutically effective amount of the crystalline Form "Z1" of O-desmethyl-venlafaxine succinate; and one or more pharmaceutically acceptable carriers, excipients or diluents.

The invention also encompasses pharmaceutical compositions comprising O-desmethyl-venlafaxine succinate of the invention. As used herein, the term "pharmaceutical compositions" includes one or more of tablets, pills, powders, liquids, suspensions, emulsions, granules, capsules, suppositories, or injection preparations.

Pharmaceutical compositions containing the O-desmethyl-venlafaxine succinate of the invention may be prepared by using diluents or excipients such as fillers, bulking agents, binders, wetting agents, disintegrating agents, surface active agents, and lubricants. Various modes of administration of the pharmaceutical compositions of the invention can be selected depending on the therapeutic purpose, for example tablets, pills, powders, liquids, suspensions, emulsions, granules, capsules, suppositories, or injection preparations.

Any excipient commonly known and used widely in the art can be used in the pharmaceutical composition. Carriers may include, but are not limited to, lactose, white sugar, sodium chloride, glucose, urea, starch, calcium carbonate, kaolin, crystalline cellulose, silicic acid, and the like. Binders may include, but are not limited to, water, ethanol, propanol, simple syrup, glucose solutions, starch solutions, gelatin solutions, carboxymethyl cellulose, shelac, methyl cellulose, potassium phosphate, polyvinylpyrrolidone, and the like.

Disintegrating agents may include, but are not limited to, dried starch, sodium alginate, agar powder, laminalia powder, sodium hydrogen carbonate, calcium carbonate, fatty acid esters of polyoxyethylene sorbitan, sodium laurylsulfate, monoglyceride of stearic acid, starch, lactose, and the like.

Disintegration inhibitors may include, but are not limited to, white sugar, stearin, coconut butter, hydrogenated oils, and the like. Absorption accelerators used include, but are not limited to, quaternary ammonium base, sodium laurylsulfate, and the like.

The novel crystalline Form Z of O-desmethyl-venlafaxine succinate can be characterized by PXRD, DSC, TGA, IR as follows:

(i) Characterization by PXRD

Analytical method: Powder X-ray Diffraction was measured by using a Rigaku D/MAX 2200 VPC diffraction meter, the powder x-ray diffraction pattern was measured at room temperature using a Cu Kα filled tube (40 kV, 40 mA) as the x-ray source with a wide-angle goniometer, a 1° scattering slit, an 1° diverging slit, a graphite secondary monochromator and a scintillation counter. Data collection was done in 2θ continuous scan mode at a scan speed of 3°/minute in scan steps of 0.02° in the range of 2° to 40°.

The XRPD peaks of crystalline anhydrous Form "Z" of O-desmethyl-venlafaxine succinate is as shown in below table:

TABLE I

| Sr. No. | 2-Theta | d(Å) | Intensity of Peak |
|---|---|---|---|
| 1 | 4.97 | 17.7 | Weak |
| 2 | 10.09 | 8.75 | Medium |
| 3 | 12.00 | 7.36 | Weak |
| 4 | 13.05 | 6.77 | Strong |
| 5 | 14.23 | 6.21 | Strong |
| 6 | 15.78 | 5.61 | V. strong |
| 7 | 16.57 | 5.34 | V. strong |
| 8 | 17.54 | 5.05 | Strong |
| 9 | 19.14 | 4.63 | Strong |
| 10 | 19.86 | 4.46 | V. strong |
| 11 | 20.30 | 4.36 | Strong |
| 12 | 21.52 | 4.12 | Weak |
| 13 | 22.23 | 3.99 | Weak |
| 14 | 23.24 | 3.82 | Medium |
| 15 | 23.62 | 3.76 | Weak |
| 16 | 24.41 | 3.64 | Weak |
| 17 | 25.82 | 3.44 | V. strong |
| 18 | 26.46 | 3.36 | Medium |
| 19 | 28.58 | 3.12 | Weak |
| 20 | 28.85 | 3.09 | Weak |
| 21 | 29.36 | 3.03 | Weak |
| 22 | 31.37 | 2.84 | Medium |
| 23 | 33.65 | 2.66 | Weak |
| 24 | 36.65 | 2.44 | Weak |
| 25 | 37.94 | 2.36 | Weak |
| 26 | 38.32 | 2.34 | Weak | weak intensity: I/Io is less than 20
medium intensity: I/Io is in between 21 to 35
strong intensity: I/Io is in between 36 to 50
v. strong intensity: I/Io is greater than 50

(ii) Characterization by Differential Scanning Calorimetry (DSC)

Analytical Method:

Differential scanning calorimetric analysis was performed using a Perkin Elmer Diamond DSC control unit and a DSC 300° C. differential scanning calorimeter. 2-5 mg samples were placed in crimped aluminum pans and heated from 50° C. to 300° C. in a liquid nitrogen atmosphere at a heating rate of 10° C./minute. Zinc-Indium was used as the standard substance.

(iii) Thermogravimetric Analysis:

Analytical Method:

Thermogravimetric analysis was performed using a Pyris1 TGA Perkin Elmer control unit and a TG/DTA 300 simultaneous differential thermal/Thermogravimetric measurement unit. 3-5 mg samples were placed in open aluminum pans and heated from 50° C. to 300° C. in a dry nitrogen atmosphere at a heating rate of 5° C./minute. Alumen was used as the standard substance.

(iv) Characterization by IR

Figure 4:
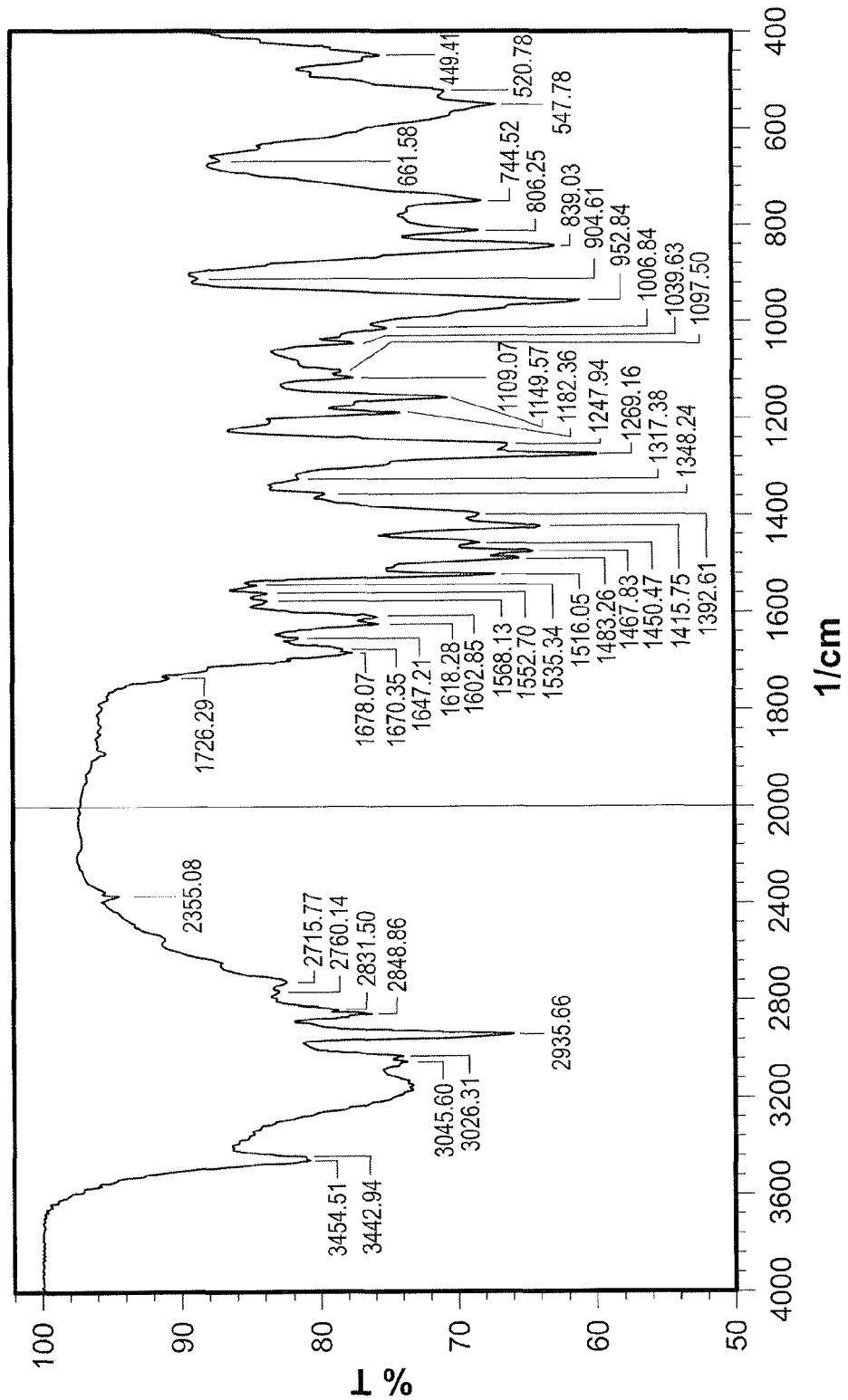
FIG. 4 represent the Fourier transform infrared spectrum of Form "Z" of O-desmethyl-venlafaxine succinate with characteristics peaks at about 3454, 2935, 2848, 1678, 1516, 1415, 1269, 1182, 1149, 952, 839, 744, and 547 cm$^{-1}$.

The IR spectrum was measured by the KBr method. FIG. 4 represents the IR spectra of Form Z of O-desmethyl-venlafaxine succinate.

The novel crystalline Form "Z1" of O-desmethyl-venlafaxine succinate can be characterized by PXRD, DSC, and solid states $^{13}$C NMR as follows:

(i) Characterization by PXRD

Analytical method: Powder X-ray diffraction was measured by using a Rigaku D/MAX 2200 VPC diffraction meter, the powder x-ray diffraction pattern was measured at room temperature using a Cu Kα filled tube (40 kV, 40 mA) as the x-ray source with a wide-angle goniometer, a 1° scattering slit, an 1° diverging slit, a graphite secondary monochromator and a scintillation counter. Data collection was done in 2θ continuous scan mode at a scan speed of 3°/minute in scan steps of 0.02° in the range of 2° to 40°.

The crystalline Form "Z1" of O-desmethyl-venlafaxine succinate is characterized by its powder X-ray diffraction pattern as shown in FIG. 7. The crystalline Form "Z1" of O-desmethyl-venlafaxine succinate is also characterized by its powder X-ray diffraction pattern having peaks expressed as 2θ at about 5.1, 10.3, 12.1, 13.3, 14.3, 15.9, 16.7, 17.7, 19.2, 20.0, 20.4, 23.3, 24.5, 25.2, 25.9, 26.7 and 31.4 degrees.

The XRPD peaks of crystalline anhydrous Form "Z1" of O-desmethyl-venlafaxine succinate is as shown in below table:

TABLE II

| Sr. No. | 2-Theta | d(Å) | Intensity of Peak |
|---|---|---|---|
| 1 | 5.12 | 17.24 | Weak |
| 2 | 10.23 | 8.63 | Weak |
| 3 | 12.15 | 7.27 | Weak |
| 4 | 13.27 | 6.66 | Medium |
| 5 | 14.29 | 6.18 | Weak |
| 6 | 14.79 | 5.98 | Weak |
| 7 | 15.92 | 5.56 | V. Strong |
| 8 | 16.71 | 5.30 | Weak |
| 9 | 17.24 | 5.13 | Weak |
| 10 | 17.67 | 5.01 | Weak |
| 11 | 18.20 | 4.86 | Weak |
| 12 | 19.15 | 4.62 | Weak |
| 13 | 19.65 | 4.51 | Weak |
| 14 | 19.99 | 4.43 | V. Strong |
| 15 | 20.44 | 4.33 | Medium |
| 16 | 21.45 | 4.13 | Weak |
| 17 | 22.39 | 3.96 | Weak |
| 18 | 22.47 | 3.95 | Weak |
| 19 | 23.34 | 3.80 | Weak |
| 20 | 23.75 | 3.74 | Weak |
| 21 | 24.39 | 3.64 | Weak |
| 22 | 25.21 | 3.52 | Weak |
| 23 | 25.76 | 3.45 | Weak |
| 24 | 26.10 | 3.41 | V. Strong |
| 25 | 26.72 | 3.33 | Weak |
| 26 | 28.36 | 3.14 | Weak |
| 27 | 28.62 | 3.11 | Weak |
| 28 | 31.46 | 2.84 | Weak |
| 29 | 32.14 | 2.78 | Weak |
| 30 | 33.73 | 2.65 | Weak |
| 31 | 35.54 | 2.52 | Strong |
| 32 | 36.55 | 2.45 | Weak |

TABLE II-continued

| Sr. No. | 2-Theta | d(Å) | Intensity of Peak |
|---|---|---|---|
| 33 | 37.14 | 2.41 | Weak |
| 34 | 37.82 | 2.37 | Weak |
| 35 | 38.35 | 2.34 | Weak |

Weak intensity: I/Io is less than 15
medium intensity: I/Io is in between 15 to 35
strong intensity: I/Io is in between 36 to 50
v. strong intensity: I/Io is greater than 50

(ii) Characterization by Differential Scanning Calorimetry (DSC)

Analytical Method:

Differential scanning calorimetric analysis was performed using a Perkin Elmer Diamond DSC control unit and a DSC 300° C. differential scanning calorimeter. 2-5 mg samples were placed in crimped aluminum pans and heated from 50° C. to 300° C. in a liquid nitrogen atmosphere at a heating rate of 10° C./minute. Zinc-Indium was used as the standard substance.

(iii) Solid-States $^{13}$C Nuclear Magnetic Resonance:

The crystalline Form "Z1" is characterized by having the following chemical shifts expressed in parts per million at about 19.9, 24.8, 27.1, 29.1, 29.7, 32.9, 35.4, 37.2, 40.7, 41.5, 43.2, 44.9, 50.0, 52.7, 55.2, 58.6, 61.0, 61.6, 62.1, 73.5, 76.6, 114.3, 126.7, 126.7, 127.7, 128.4, 131.4, 132.1, 155.2 and 179.0.

The process of the present invention will be explained in more detail with reference to the following examples, which are provided by way of illustration only and should not be constructed as limit to the scope of the claims in any manner.

EXAMPLES

Example-1

Preparation of Venlafaxine Free Base from Venlafaxine Hydrochloride Form-II 1.0 Lt assembly arranged in a plastic tub, 100 g venlafaxine HCl & 200 mL water charged at 25-35° C. and stirred for 10-15 minutes up to clear solution followed by addition of 10% NaOH solution drop by drop till pH of the reaction mixture was achieved 12 to 13 on pH paper. Then 200 ml MDC was added and stirred for 30 minutes. Settled for 15-30 minutes. Organic layer and aqueous layer were separated out. Further 200 ml of MDC was charged in aqueous layer. Stirred for 30 minute and settled for 15-30 minutes. Organic layer and aqueous layer was Separated out. Organic layer was dried over anhydrous Na$_2$SO$_4$ and filtered through cotton and washed with 100 ml MDC. Distilled out MDC layer atmospherically at 45-50° C. and high vacuum applied at 45-50° C. Taken out the solid residue and dried it at 50-55° C. Dry wt: 80-84 g.

Example-2

Preparation of O-Desmethyl-Venlafaxine Free Base from Venlafaxine Free Base 50 g Venlafaxine Base, 61.8 g sodium salt of thiophenolate, 230 mL DMF were charged in to RBF and heated to get 155° C.±5° C., maintained till TLC complies (approx. 12-15 hours). Then cooled to 50° C., followed by the distillation of DMF by high vacuum to obtain the solid and cooled to room temperature at about 25° C. to 35° C. 300 mL water was added and stirred till free solution was obtained. 100 mL ethyl acetate was added, and then concentrated HCl was added to adjust the pH 3.5. Stirred for 30 minutes at 25° C. to 35° C. The layer was separated and further 100 ethyl acetate was added to the aqueous layer, stirred for 30 minute, then separated out. Charcoal was added to the aqueous layer, stirred for 60 minutes at 25° C. to 35° C. Filtered off and washed with 25 mL water. Then liq. ammonia was added to adjust pH 9.5-9.0, stirred for 30 minutes, filtered and washed with 50 mL water. Wet Cake: 48 g approx. Dry for 50-60° C. for 8-10 hrs. Dry wt: 45.0 g Example-3

Preparation of O-Desmethyl-Venlafaxine Freebase from Venlafaxine Hydrochloride Form-II 1 Kg Venlafaxine Hydrochloride Form-II, 0.510 Kg sodium hydride, 3 L DMF were charged in to RBF at 0° C. to 10° C. with continuous stirring. 0.60 Kg ethanethiol solution in 1 L DMF was gradually added to the reaction mixture at same temperature and heated to 140° C. for 7 hours. After the completion of the reaction by TLC, the reaction mixture was cooled to 35° C. and treated with 10 L water. The reaction mixture was further treated with 1.55 L hydrochloric acid to adjust the pH 2.0 to 3.0 at same temperature and charcoalized with 0.050 Kg charcoal with stirring for 30 min. The reaction mixture was filtered and layers were separated. The aqueous layer was treated with 1.0 L sodium hydroxide solution in 1 L water to adjust the pH to 8.5 to 9.0. The precipitated product was filtered and washed with water.

Wet Cake: 1.90 Kg approx. Dry for 60-70° C. for 12 hrs. Dry solid and 5 L methanol were heated at 65° C. for 30 min. The reaction mixture was cooled at 35° C. within 3 hours. The product was filtered and washed with methanol. Wet Cake: 1.80 Kg approx. Dry for 60-70° C. for 12 hrs to obtain 92% O-desmethyl-venlafaxine free base crystalline Form-A.

Example-4

Preparation of O-Desmethyl-Venlafaxine Succinate from O-Desmethyl-Venlafaxine Free Base (Reference Example from U.S. Pat. No. 6,673,838 B2)

A 5 L multi-necked flask, equipped with a stirrer, a thermometer, and a condenser, with a nitrogen inlet attached to a Firestone valve were placed in a heating mantle. The system was purged with nitrogen and a nitrogen atmosphere was maintained. 1.668 kg (2111 mL) acetone and 0.667 kg (667 mL) water were charged into the flask. The stirrer was started and 0.250 kg (0.949 mol) O-desmethyl-venlafaxine free base were added. The suspension was stirred for 30 minutes. 0.1155 kg (0.978 mol) succinic acid was added and the transfer was completed with rinses of acetone (0.186 kg, 236 mL) and water (0.075 kg, 75 mL). The suspension was stirred, warmed to 60° C. (±3° C.), and maintained at 60° C. (±3° C.). While being stirred for 30-60 minutes. A clear to cloudy solution was obtained. The mixture was then filtered through a filter comprised of polypropylene cloth with a filter paper underlay into a 5 L multi-necked flask equipped with a mechanical stirrer, a thermometer, and a condenser fitted with a vacuum outlet. The filter funnel was rinsed with warm (50-60° C.) aqueous acetone (24:76 v/v, 427 mL). The system was purged with nitrogen and the solution was cooled to 30-35° C. to induce crystallization. The stirred slurry of crystals was maintained at that temperature for about 4 hours. The stirred slurry of crystals was cooled to 0-5° C. and maintained at that temperature for about 1 hour. The crystals were collected on a polypropylene cloth filter with a filter paper underlay in a 15 cm funnel. The filter cake was washed with cold (0-5° C.) aqueous acetone (24:76 v/v, 2.times.300 mL) and filtered for 5 minutes. A dam was formed on top of the filter with a sheet of latex rubber. An aspirator was applied to the filter cake for 1 hour. The weight of the filter cake was about 0.351 kg. The product was dried under vacuum (50 mm Hg) at 30±5° C. for 12 hours. The product was then dried under vacuum (50 mm Hg) at 45±5° C. for 24 hours.

Example-5

Preparation of O-Desmethyl-Venlafaxine Succinate Form "Z"

20.0 g of O-desmethyl-venlafaxine free base crystalline Form-A (substantially anhydrous) and 9.0 g succinic acid (substantially anhydrous) were taken in a clean and dry grinder apparatus at 25° C. to 35° C. The solid-solid mixture was grinded at 50-55° C. for about 1 to 2 minutes. After grinding, the solid-solid mixture was cooled to 38° C.-42° C. Again the mixture was grinded to 50-55° C. with exothermicity. The above process was repeated for about 25-35 cycles till O-desmethyl-venlafaxine free base and succinic acid mixture is converted to O-desmethyl-venlafaxine succinate crystalline Form Z as monitored by X-ray powder diffraction.

The product was unloaded from the grinder. Crystalline Form Z was confirmed by characterization with X-ray powder diffraction substantially as depicted in FIG. 1. HPLC Purity: 99.94%.

Characteristic Physical properties:
Melting point: 109-110° C.
Moisture content (%) by KF): 3.50%
DSC: Endothermic peak at 103.23° C.
TGA: 3.08%.

Example-6

Preparation of O-Desmethyl-Venlafaxine Succinate Form "Z1"

1.4 Kg O-desmethyl-venlafaxine free base crystalline Form-A (substantially anhydrous) and 0.63 Kg succinic acid (substantially anhydrous) were taken in a clean and dry multi-mill under having controlled humidity conditions, having relative humidity in the range of 50±10%. All the blades and scrappers were arranged to be moved in sharper edge side i.e. clock-wise direction. The multi-mill grinder was started and solid-solid mixture was grinded for 1 to 2 minutes at below 60° C. After grinding, the solid-solid mixture was cooled below 60° C. Again the mixture was grinded for 1 to 2 minutes at below 60° C. with exothermicity. The above process was repeated for about 25-35 cycles till O-desmethyl-venlafaxine free base and succinic acid mixture was converted to O-desmethyl-venlafaxine succinate crystalline Form Z1 as monitored by X-ray powder diffraction. The product was unloaded from the grinder. Crystalline Form Z1 was confirmed by characterization with X-ray powder diffraction substantially as depicted in FIG. 7 and solid states 13C NMR as depicted in FIG. 9.

HPLC Purity: 99.99%.
Characteristic Physical properties:
Moisture content (%) by KF): 1.39%
DSC: Endothermic peak at 97° C.
TGA: 1.50%.
Elemental Analysis: % C: 62.21; % H: 8.71; % N: 3.62.

Example 7

Packing of Crystalline Form "Z" or "Z1" of O-Desmethyl-Venlafaxine Succinate

The crystalline form of O-desmethyl-venlafaxine succinate obtained in example-5 or example-6 were stored under nitrogen atmosphere and packed in a non-permeable bag tied with a thread, keeping primary packing inside a black color polyethylene bag containing oxygen busters and sealing it, placing above the non-permeable bag inside a triple laminated bag containing oxygen busters and sealing it, and placing the sealed triple laminated bag inside a closed high density polyethylene (HDPE) container.

The storage stability of crystalline Form "Z" after storage for 3 months at 40° C. and a relative humidity of 75% or at 25° C. and a relative humidity of 60% shows water content NMT 3.0% and no detectable amount of crystalline Form-I or Form-II by X-ray powder diffraction.

The storage stability of crystalline Form "Z1" after storage for 3 months at 40° C. and a relative humidity of 75% or at 25° C. and a relative humidity of 60% shows water content NMT 1.5% and no detectable amount of crystalline Form-I or Form-II by X-ray powder diffraction.

While the present invention has been described in terms of its specific embodiments, certain modifications and equivalents will be apparent to those skilled in the art and are intended to be included within the scope of the present invention.

The invention claimed is:

1. A crystalline Form Z1 of O-desmethyl-venlafaxine succinate characterized by:
    (a) a solid state $^{13}C$ nuclear magnetic resonance having the following chemical shifts expressed in parts per million at about 19.9, 24.8, 27.1, 29.1, 29.7, 32.9, 35.4, 37.2, 40.7, 41.5, 43.2, 44.9, 50.0, 52.7, 55.2, 58.6, 61.0, 61.6, 62.1, 73.5, 76.6, 114.3, 126.7, 127.7, 128.4, 131.4, 132.1, 155.2 and 179.0;
    (b) a water content of about 1.0% to about 2.0% w/w, when analyzed by Karl Fischer method; and
    (c) a powder XRD pattern having peaks 5.1, 10.3, 12.1 13.3, 14.3, 15.9, 16.7, 17.7, 19.2, 20.0, 20.4, 23.3, 24.5, 25.2, 25.9, 26.7 and 31.4 degrees (±0.2° 2θ).

2. A process for the preparation of crystalline Form Z1 of O-desmethyl-venlafaxine succinate as claimed in claim 1, the process comprising the steps of:
    (a) adding a solid-solid mixture of O-desmethyl-venlafaxine free base and succinic acid in a grinder; and
    (b) grinding the solid-solid mixture under controlled humidity to obtain the crystalline Form Z1 of O-desmethyl-venlafaxine succinate.

3. The process according to claim 2, wherein the grinding of the solid-solid mixture is carried out in the absence of solvents.

4. The process according to claim 2, wherein the controlled humidity is a relative humidity in the range of 50±10%.

5. The process according to claim 2, wherein the grinding of the solid-solid mixture is carried out at a temperature below 60° C.

6. The process according to claim 2 further comprising repeating the grinding cycle one or more times.

7. The process according to claim 2, wherein the grinder comprises one or more of small-scale to large-scale mixer grinder which can prepare the homogenous mixture of two solids.

8. The process according to claim 7, wherein the grinder comprises one or more of mixers, mills, blenders, and micronizers.

9. The process according to claim 7, wherein the mixer is selected from one or more of a common mixer grinder, a batch mixer, a continuous mixer, and an intensive mixer.

10. The process according to claim 9, wherein the batch mixer is a change-can mixer, helical-blade mixer, or a double-Arm Kneading mixer.

11. The process according to claim 8, wherein the mill comprises one or more of a multi-mill, jet-mill, ball-mill, hammer mill, roller mill, gyratory mill, Of and a quadro dry mixing apparatus.

12. A pharmaceutical composition comprising a therapeutically effective amount of crystalline Form Z1 of O-desmethyl-venlafaxine succinate as claimed in claim 1 and one or more pharmaceutically acceptable carriers, excipients, or diluents.

13. The crystalline form Z1 of O-desmethyl-venlafaxine succinate according to claim 1, further characterized by a powder XRD pattern as set out in FIG. 7.

14. The crystalline form Z1 of O-desmethyl-venlafaxine succinate according to claim 1, further characterized by a differential scanning calorimetry endotherm curve as set out in FIG. 8.

15. The crystalline form Z1 of O-desmethyl-venlafaxine succinate according to claim 1, further characterized by a solid state $^{13}C$ nuclear magnetic resonance spectrum as set out in FIG. 9.

16. The crystalline form Z1 of O-desmethyl-venlafaxine succinate according to claim 1 further characterized by a differential scanning calorimetry thermogram showing endothermic peak at 97.24° C.

* * * * *